Figure 1:
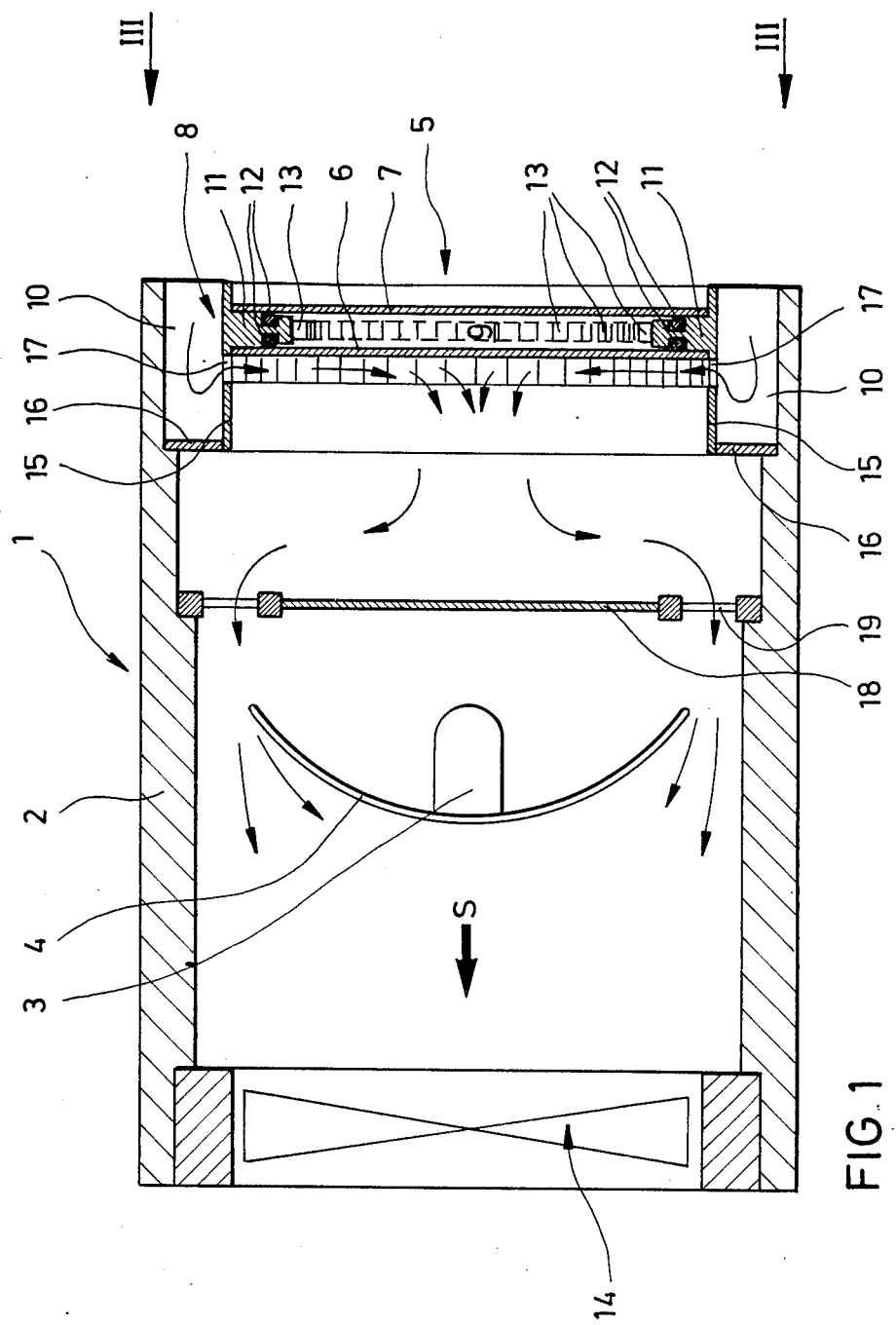

United States Patent [19]
Greutert

[11] Patent Number: 4,939,374
[45] Date of Patent: Jul. 3, 1990

[54] IRRADIATION DEVICE

[75] Inventor: Albert Greutert, Sachseln, Switzerland

[73] Assignee: Maxs AG, Sachseln, Switzerland

[21] Appl. No.: 258,288

[22] Filed: Oct. 14, 1988

[30] Foreign Application Priority Data

Oct. 16, 1987 [DE] Fed. Rep. of Germany ... 8713930[U]

[51] Int. Cl.⁵ .............................................. H01K 1/26
[52] U.S. Cl. ............................. 250/504 R; 250/503.1; 250/505.1; 350/1.5; 350/312; 350/318
[58] Field of Search ............ 250/504 R, 504 H, 503.1, 250/505.1; 350/1.5, 312, 318

[56] References Cited

U.S. PATENT DOCUMENTS 4,546,420 10/1985 Wheeler et al. .................. 362/268

FOREIGN PATENT DOCUMENTS

| 496992 | 1/1978 | Australia . | |
|---|---|---|---|
| 765042 | 8/1967 | Canada | 250/505.1 |
| 0073669 | 3/1983 | European Pat. Off. . | |
| 692907 | 6/1940 | Fed. Rep. of Germany . | |
| 8628453 | 3/1987 | Fed. Rep. of Germany . | |
| 743499 | 12/1943 | Fed. Rep. of Germany . | |
| 896395 | 11/1953 | Fed. Rep. of Germany . | |
| 911525 | 5/1954 | Fed. Rep. of Germany . | |
| 812549 | 5/1937 | France | 350/1.5 |
| 271991 | 7/1951 | Switzerland | 350/1.5 |
| 1084335 | 9/1967 | United Kingdom . | |
| 1201607 | 8/1970 | United Kingdom | 350/312 |

Primary Examiner—Jack I. Berman
Attorney, Agent, or Firm—James D. Hall

[57] ABSTRACT

An irradiation device which includes a radiation source arranged within a housing and a filter arranged in the ray path of the radiation source which consists of two transparent, essentially plane-parallel discs. The discs are held in a frame and a medium which selectively influences the spectrum of the rays of the radiation source is provided between the discs. A plurality of outwardly projecting cooling fins are arranged on the outer circumference of the frame and serve in conjunction with the medium between the disc and the frame to dissipate heat from the medium.

23 Claims, 7 Drawing Sheets

IRRADIATION DEVICE

The present invention refers to an irradiation device comprising a radiation source arranged within a housing as well as a filter arranged in the ray path and consisting of two transparent, essentially plane-parallel discs, which are held in a frame, a medium which selectively influences the spectrum of the rays being provided between the discs.

Such an irradiation device is known e.g. from German-pat. No. 896 395. The irradiation device shown in said patent is used for thermotherapy of the human body. In most cases, the radiation spectrum emitted by the radiation source is not suitable as a whole for use in the case of thermotherapy. Hence, a filter is placed in front of the radiation source so as to filter specific bands out of the radiation spectrum. In view of the fact that the filter is arranged in the ray path of the radiation source, it is also subjected to extremely high temperatures. The known irradiation device attempts to avoid excessive heating of the medium contained within the filter by providing a filter which has an appropriately large diameter and which is, consequently, capable of taking up a larger amount of heat. Since, however, the filter continues to heat up, the irradiation device must be switched off after a specific period of operation. If such switching off is not carried out, the filter will be destroyed. The known irradiation device is disadvantageous in so far as it can only be used for a specific period and in so far as, due to the large diameter of the filter, the whole device requires very much space.

German-pat. No. 911 525 describes an irradiation device in the case of which an additional disc is arranged on the filter for the purpose of forming a liquid-tight space, which will collect liquid, if one of the discs enclosing the medium shatters due to excessive temperatures. The medium, in most cases water, is then collected in the other space and discharged through a discharge tube.

German-pat. No. 743 499 describes an irradiation device in the case of which a water filter enclosed between two discs is provided. The frame is provided with an inlet and an outlet so that the temperature of the filter can be reduced by exchanging the water within the filter. Furthermore, German-pat. No. 692 907 describes an irradiation device with a water filter in the case of which cooling tubes extending through the water filter are arranged between the discs of the water filter.

Although, other than in the case of a direct introduction of cooling water into the water filter, this type of cooling permits a temperature which is as uniform as possible within the water filter, the known device shows the disadvantage that the tubes are arranged within the ray path of the irradiation device and that, consequently, said tubes impair the efficiency of the device. Moreover, it is necessary to provide a storage receptacle for cooling water and, in addition, a cooling device.

Finally, German Utility Model G 86 28 453 discloses an irradiation device of the type mentioned at the beginning, in the case of which the water filter, which is constructed after the fashion of a cavity cuvette, has an outlet at its uppermost point so that gas or vapour bubbles, which may possibly be released and which form larger bubbles in the liquid-containing space, can develop. The water filter is also provided with an inlet so that the water filter, when in operation, can be connected to a coolant circuit.

Especially in cases in which glass discs are used, such a water circuit cannot only cause shattering of said glass discs but it also requires an enormous amount of apparatus.

Hence, the present invention is based on the task of improving an irradiation device of the type mentioned at the beginning in such a way that an effective cooling of the filter is achieved with the least possible expenditure.

In accordance with the present invention, this task is solved by the features that outwardly projecting cooling fins are arranged on the outer circumference of the frame.

It is true that Australian application No. 496 992 discloses a miner's lamp whose housing carries external cooling fins at the front end thereof, but these cooling fins are used for dissipating heat from the housing; they are, however, not used for cooling a filter. In the case of this miner's lamp, glass discs are provided, which, for avoiding thermal stress, are not fixedly held in the frame. Nor is it necessary to cool said glass discs, since they will easily withstand higher temperatures as long as the heat is distributed somewhat uniformly over the glass disc.

On the basis of the embodiment according to the invention, the frame, which communicates with the medium, dissipates heat to the surroundings via the cooling fins. This permits, also in the case of prolonged operation of the irradiation device, a state of equilibrium on the basis of which the irradiation device can be operated also for longer periods.

A frame which is made of metal or of some other material having a good thermal conductivity will support an effective cooling of the filter.

Without impairing a good transmission of heat, the frame can, in an advantageous manner, be provided with a two-piece structural design comprising an outer frame member, which supports the cooling fins, and a changing frame, which is replaceably held in said outer frame member and which has secured thereto the filter discs. The transmission of heat will be good in view of the fact that the separation between the replaceable filter and the housing is carried out at the frame, which can consist of a material having good thermal conductivity. If the discs themselves were made replaceable, this would always entail the problem that the transmission of heat to the frame may possibly deteriorate.

The transmission of heat between the filter medium and the frame is supported by the fact that the frame has an inwardly projecting, circumferentially extending support shoulder, said support should projecting between the discs and said discs abutting on said support shoulder. Hence, one area of the frame which has a good thermal conductivity extends directly up to the medium.

It will be particularly advantageous when the support shoulder has provided therein a circumferentially extending cooling groove, which is open towards the interior space between the discs. This has the effect that the support shoulder is practically formed such that two cooling fins are defined, whereby the contact surface contacting the medium between the two discs is substantially enlarged. Due to this surface enlargement, it is possible to dissipate such an amount of heat that the frame temperature increases to such an extent that, in favourable cases, the outer cooling fins can be dispensed with. Hence, independent protection is claimed for this embodiment.

The support shoulder surface facing towards the filter medium can be enlarged still further by providing two cooling grooves side by side, said cooling grooves being separated by a cooling web. The overall number of cooling grooves which is to be provided depends not least on the distance between the two discs.

The cooling groove has a depth which is preferably at least equal to that of the support shoulder.

It will be advantageous when the cooling groove has a V-shaped or a U-shaped groove base. This has the effect that the remaining cooling fins enlarge towards the frame so that a uniform heat flow can develop.

In connection with the cooling groove, it will be advantageous when the discs are each held by a press ring pressing the respective disc against one side of the support shoulder. This press ring permits the disc to be fastened to the support shoulder without there being any necessity of providing a hole in said support shoulder for receiving therein a fastening screw.

Without impairing the transmission of heat, the sealed space containing the filter medium can be sealed in a particularly simple manner by providing the discs with a bevel on their respective outer edge facing the support shoulder and by arranging a sealing ring between said bevel and said support shoulder.

Fastening the discs of the filter to the frame by means of screws can be dispensed with in an advantageous manner, when the outer edge of a press ring facing away from the respective disc is slightly bevelled and when a circumferentially extending groove is provided in the outer end face of the frame, which surrounds the press rings, in such a way that a crimped web is left. After insertion of the press ring, this web only has to be crimped inwards, where it will then engage behind the bevel of the press ring and maintain said press ring in a position where it is pressed against the disc. An intimate contact between the press ring and the frame is thus achieved, and this enhances the conduction of heat and, consequently, the dissipation of heat from the filter.

It will also be particularly advantageous when the discs consist of plastic material. In contrast to glass discs, discs of plastic material have the possibility of bulging slightly after the fashion of a diaphragm when the filter medium, e.g. water, is heated so that inadmissible pressure peaks cannot occur in the interior of the filter. Discs of polycarbonate proved to be particularly useful.

Another advantageous possibility of effecting a better dissipation of the heat from the medium will be obtained when the frame has attached thereto lamellae, which extend inwards between the discs and which are immersed in the medium.

If good cooling of the filter is to be achieved also in the case of a compact structural design of the irradiation device, it will be advantageous when the housing is substantially tubular and when the frame has the outer ends of its cooling fins inserted into the housing such that air flow openings are kept free. The housing, when in an upright position, produces an effect similar to that of a chimney and supports a flow of cool air round the cooling fins.

A good flow of air round the cooling fins can also be achieved, in a structurally simple manner, by providing a fan in the housing. It is thus possible to use the irradiation device — also one having a compact structural design — in any position without causing excessive heating of the filter.

In accordance with an advantageous embodiment of the invention, the fan is arranged on the side of the radiation source facing away from the filter. This has the effect that the fan will first suck in fresh air via the cooling fins of the filter into the tubular housing, the air, which has already been slightly heated, serving also to cool down the radiation source.

Especially in cases in which the discs enclosing the medium within the filter are made of a plastic material, it will be advantageous when an annular flow deflection means is arranged concentrically with the housing between the disc of the filter facing the radiation source and said radiation source, the flow inlet of said flow deflection means facing the cooling fins of the frame, whereas its flow outlet is directed towards the filter. This has the effect that, after having passed the cooling fins, the air entering the housing will be directed onto the disc facing the radiation source, whereby the disc in question will be cooled in an advantageous manner.

A particularly gentle deflection of the cooling air and, consequently, an effective cooling with minor flow losses can be achieved by providing the feature that the flow deflection means has the structural design of a torus half whose outer edge abuts on the inner wall of the tubular housing and whose inner edge is directed towards the filter.

A flow deflection means which is particularly simple from the structural point of view can be achieved by providing the features that the cooling fins are lengthened towards the interior of the housing and that the flow deflection means is constructed as a cylindrical ring connecting the base portions of the cooling fins, said ring being closed with respect to the housing by means of a flange member and being arranged in spaced relationship with the inner disc of the filter so as to form the flow outlet. This has the advantage that the flow deflection means can be cast in one piece with the frame and the cooling fins. Moreover, the lengthened cooling fins effect a still better dissipation of heat.

It will also be advantageous when a heat-resistant glass plate is arranged concentrically with the housing between the radiation source and the filter, the edge of said glass plate being spaced from the inner wall of the housing by means of an essentially closed annular gap. This glass plate fulfills a double function. On the other hand, it protects the filter against an excessive development of heat. On the other hand, it defines an additional flow deflection means for the air entering the device via the cooling fins and the first flow deflection means. This has the effect that the incoming air sweeps along the filter disc, which faces the radiation source, for a particularly long period of time.

This effect can be intensified by providing the feature that the inner diameter of the annular gap exceeds the diameter of the inner edge of the flow deflection means. This has the effect that the air flowing radially inwards along the inner disc is deflected by 180° so that, subsequently, this air is forced to flow radially outwards. The cooling air is thus mixed well and this will positively influence the exchange of heat and, consequently, the dissipation of heat by the cooling air.

In accordance with a simple structural embodiment of the present invention, the radiation source is a halogen lamp with a reflector directed towards the filter.

Figure 2:
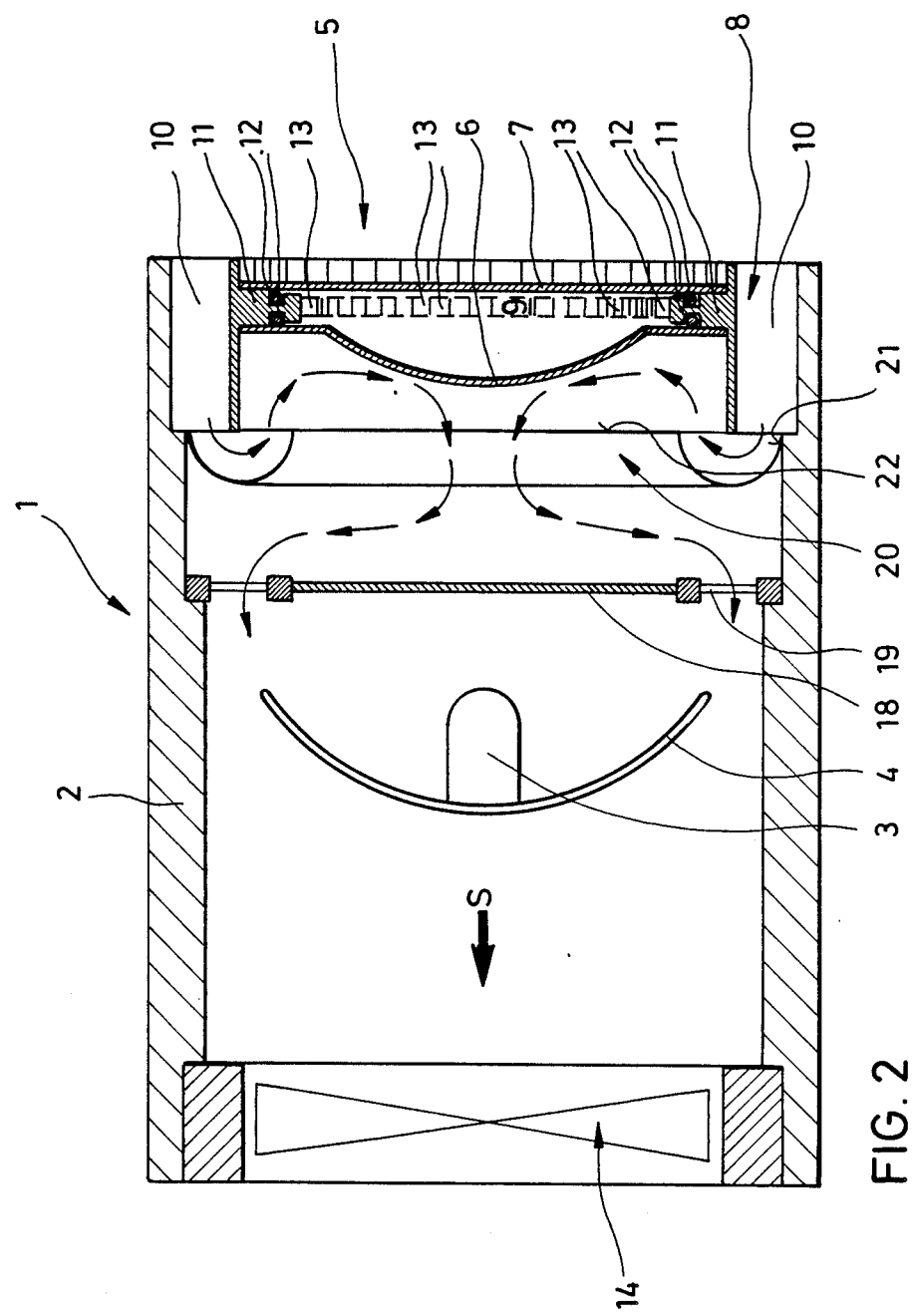
Figure 3:
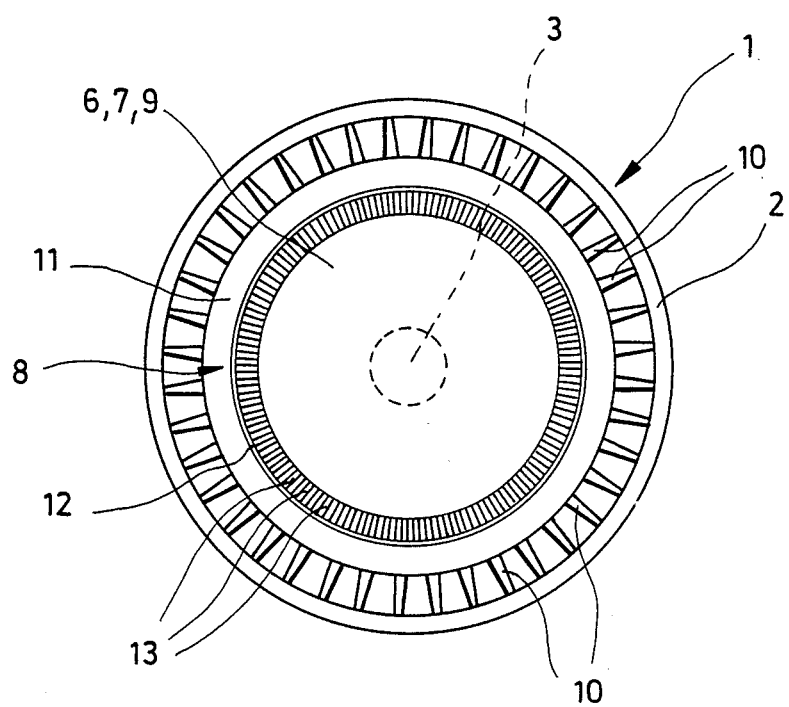
Figure 4:
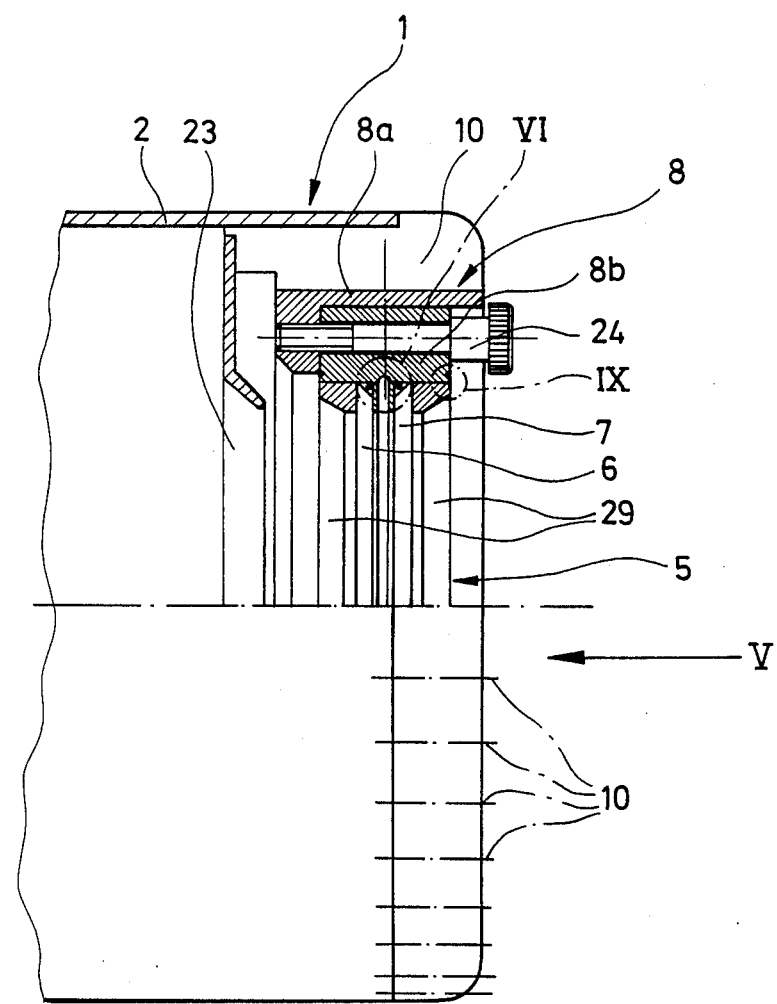
Figure 5:
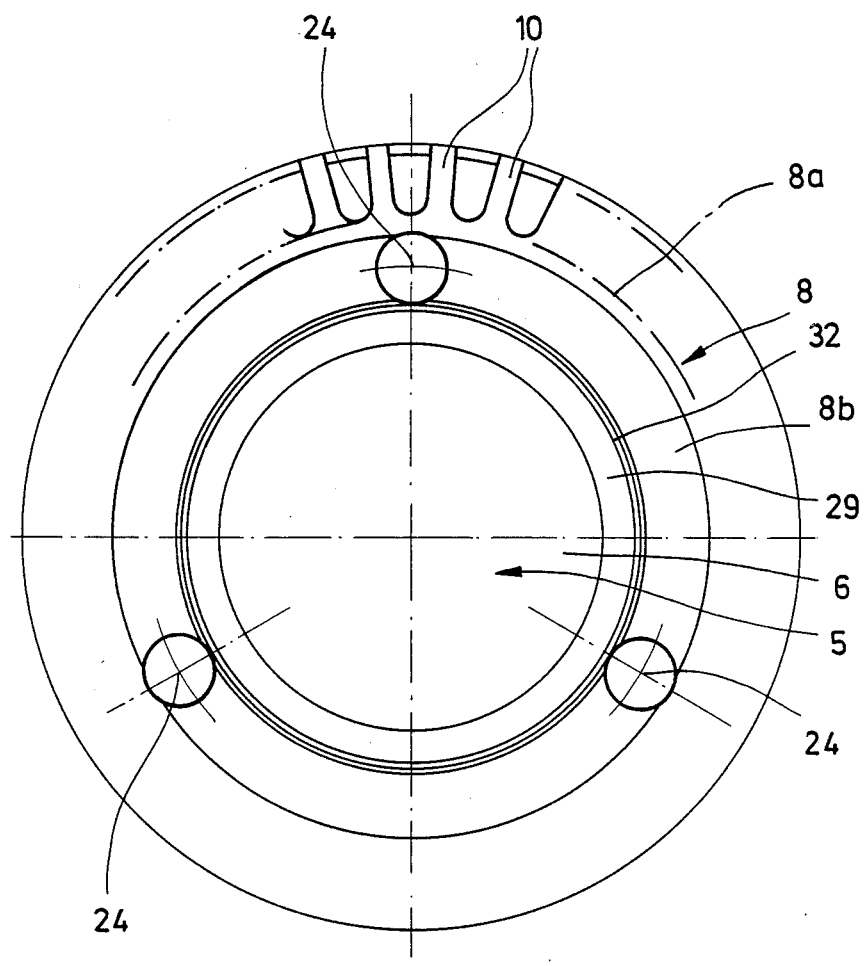
Figure 6:
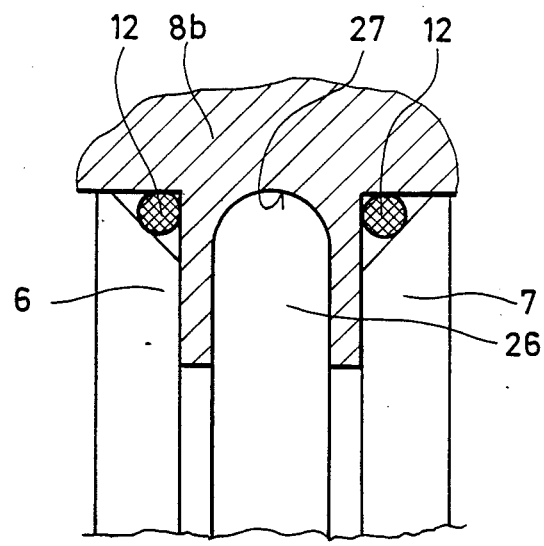
Figure 7:
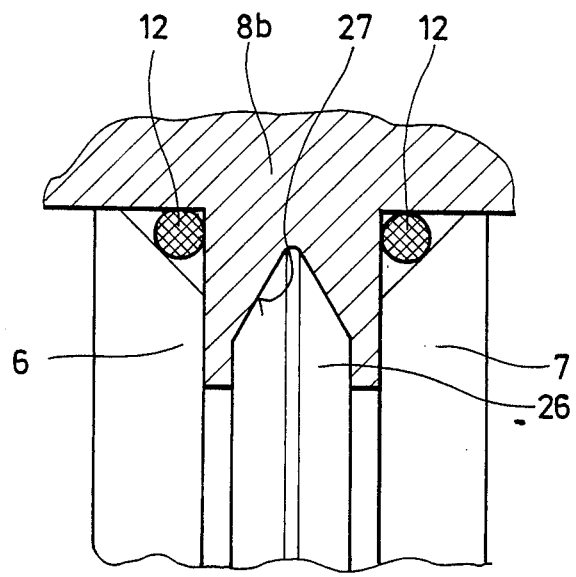
Figure 8:
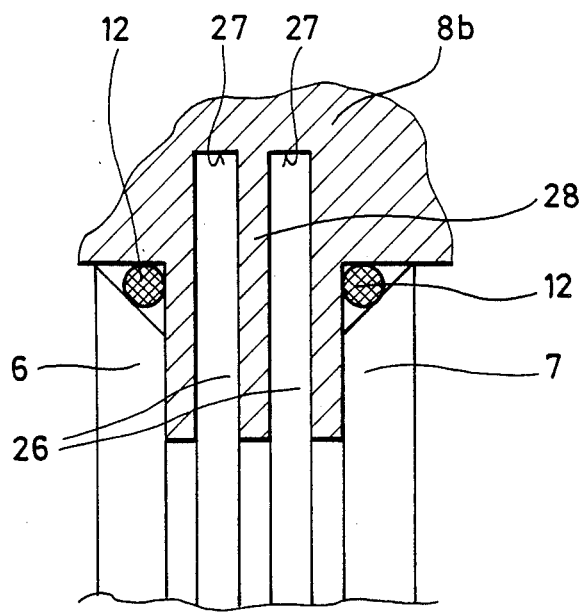

In the following, embodiments of the present invention will be explained in detail on the basis of a drawing, in which:

FIG. 1 shows, in a schematic longitudinal section, a first embodiment of an irradiation device according to the invention, FIG. 2 shows a second embodiment of an irradiation device according to the invention, the view being similar to that shown in FIG. 1, FIG. 3 shows a view of the irradiation device of FIG. 1 in the direction of the arrow III, FIG. 4 shows the front part of an irradiation device according to a third embodiment, partially in a longitudinal section, FIG. 5 shows a view of the irradiation device of FIG. 4 in the direction of the arrow V, FIG. 6 shows a view of a detail VI of FIG. 4 according to a first variant, FIG. 7 shows, in a view similar to that shown in FIG. 6, the detail according to a second variant, FIG. 8 shows, in a view similar to that shown in FIG. 6, the detail according to a third variant, and

Figures 9A, 9B:
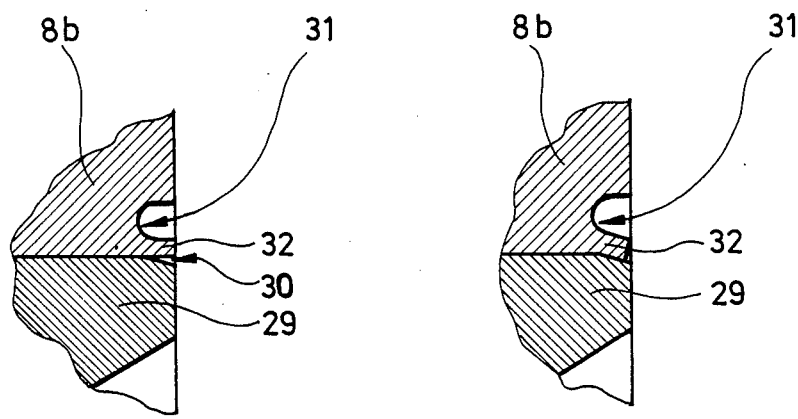

FIG. 9a,

FIG. 9b show the detail IX of FIG. 4 in one case prior to fastening by the crimped web and in one case subsequent to fastening by the crimped web.

FIG. 1 and 3 show an irradiation device 1 provided with a radiation source 3 in the form of a halogen lamp, which is arranged in a housing 2 and behind which a reflector 4 is provided. The ray path of the halogen lamp 3 has arranged therein a filter 5. The filter 5 consists of two planeparallel plastic discs 6 and 7 which are made of polycarbonate. The two plastic discs 6 and 7 are held in spaced relationship with each other by means of a frame 8 and they include a hollow space 9, which is filled with water. The water within the hollow space 9 influence the spectrum of the rays, which are emitted by the halogen lamp 3, by filtering out rays having wavelengths of from 1,300 to 1,600 nm in cooperation with the two polycarbonate discs 6 and 7. These wavelengths are wavelengths which are absorbed to a high extent by the tissue of the body and which are, consequently, less suitable for thermotherapy.

The outer circumference of the frame 8 is provided with outwardly projecting cooling fins 10, which are integrally connected to the rest of the frame 8.

A web 11 extends radially inwards from the outer circumference of the frame 8, the two discs 6 and 7 abutting on said web. On both sides of the web 11 axial grooves are provided, which have inserted therein a sealing ring 12 providing a sealing effect between the two discs 6 and 7 and the web 11. Lamellae 13, which are directed further radially inwards, extend from the web 11, said lamellae being immersed in the water contained in the hollow space 9.

The structural design of the housing 2 is essentially that of a hollow cylinder, the filter 5 having the outer ends of the cooling fins 10 of its frame 8 inserted into the housing 2. Strictly speaking, the filter 5 is located at one end face of the housing 2.

A fan 14 is arranged on the halogen lamp side which faces away from the filter 5, said fan, when in operation, sucking in air in the direction of the arrow S.

In the area of the cooling fins 10, the frame 8 is constructed in such a way that it forms a flow deflection means. For this purpose, a cylinderlike ring 15 is secured to the underside of the cooling fins 10 which project into the interior of the housing, said ring having an end face which faces the interior of said housing and which is sealed against the housing 2 by means of a flange member 16. A gap 17 remains between the filter 6 and the ring 15, said gap being only interrupted by the cooling fins 10 extending therebeyond. The result of this arrangement is that the flow deflection means, which is formed by the ring 15 and the flange member 16, comprises a flow inlet facing the cooling fins 10 and a flow outlet which consists of the gap 17 and which faces the disc 6.

A heat-resistant glass plate 18 is arranged between the halogen lamp 3 and the filter 5, the edge of said glass plate being spaced from the inner wall of the housing 2 by means of a substantially closed annular gap 19. The annular gap 19 is only interrupted by holding means for the glass plate 18.

FIG. 1 shows clearly that the thickness of the filter 5 corresponds to approximately one third of the length of the cooling fins 10 and that the cooling fins 10 are lengthened towards the interior of the housing.

In the following, the mode of operation of the embodiment according to FIG. 1 and 3 will be explained in detail.

For putting the irradiation device 1 into operation, the halogen lamp 3 and the fan 14 are first switched on. The halogen lamp emits, focussed by the reflector 4, rays in the direction of the filter 5. These rays first impinge on the heat-resistant glass plate 18 and then on the filter 5. This has the effect that the plastic discs 6 and 7 as well as the water contained in the hollow space 9 become warm, although the heat-resistant glass plate 18 retains part of the heat. Via the lamellae 13 immersed in the water, the water heated within the hollow space 9 will transmit the heat to the aluminum frame 8 and its cooling fins 10.

In view of the fact that the fan operates, air will be sucked in along the cooling fins 10, said air flowing in the direction of the arrows around the filter radially inwards along the inner plastic disc 6 thus cooling said disc 6. From this point the air flows through the annular gap 19 to the fan 14 and from said fan into the open air.

In the following, the embodiment according to FIG. 2 will be explained in detail. The structural design of the irradiation device shown in FIG. 2 is, fundamentally, the same as that described in the case of FIG. 1.

Hence, identical reference numerals are used for structural components producing the same effect. Moreover, only the differences existing with regard to the irradiation device according to FIG. 1 will be described.

In the case of the embodiment according to FIG. 2, the inner plastic disc 6 is provided with a convex curvature, whereby additional focussing of the rays emitted by the halogen lamp 3 can be achieved.

In the case of the second embodiment, the flow deflection means is a torus half 20 whose outer edge 21 abuts on the inner wall of the housing 2. The inner edge 22 of the torus half 20 faces the disc 6.

It is evident that the torus half 20 follows directly the cooling fins 10 of the frame 8. In addition, the diameter of the inner edge 22 of the torus half 20 is smaller than the internal diameter of the annular gap 19.

The mode of operation of the irradiation device according to the second embodiment is, in principle, the same as that of the irradiation device which has already been described hereinbefore. However, a special feature is to be seen in the fact that, due to the gentle deflection of the stream of air by the torus half 20 and the convex curvature of the disc 6 in connection with the diameter differences between the inner edge 22 of the torus half 20 and the inner diameter of the annular gap 19, the cooling air is utilized in a particularly efficient manner, especially for cooling the disc 6.

It is also worth mentioning that the stream of air caused by the fan 14 also has the effect that the halogen lamp 3 is cooled.

The plastic discs 6 and 7 consist of polycarbonate and can also be dyed so as to filter out specific other wavelengths of the spectrum of rays. And it is just as well possible to use a salt solution instead of water as a medium. It is also possible to provide two convex discs instead of one convex disc. The lamellae may also be provided in the form of one single annular lamella. The water within the hollow space 9 may be dyed or it may have added thereto other substances influencing the spectrum of rays.

FIG. 4 to 9 show a third embodiment of an irradiation device 1 according to the present invention.

The third embodiment essentially corresponds to the two embodiments described hereinbefore, and, consequently, identical reference numerals are used for identical and similar structural components. In the following, only the essential differences will be discussed.

As will be clearly evident from FIG. 4, the filter 5 is constructed as an interchangeable filter, the frame 8 consisting of two frame halves 8a and 8b. The outer frame member 8a carries the cooling fins 10 through which it is connected to the housing 2. At the inner end of the cooling fins 10, an air guide plate 23 is arranged, said air guide plate being similar to the torus half 22. The outer frame member 8a is provided with a concentric recess having inserted therein the inner frame member, viz. the changing frame 8b. The changing frame 8b can be screwed onto the outer frame 8a by means of knurled screws 24.

The changing frame 8b is provided with a support shoulder 25, which projects radially inwards and on the outer sides of which the two discs 6 and 7 abut. The support shoulder 25 has formed therein a circumferentially extending groove 26 which is open radially inwards.

In FIG. 6 to 8, three variants of the support shoulder are shown in detail.

The first variant of the support shoulder 25, which is shown in FIG. 6, is provided with only one groove 26 whose depth corresponds to that of the support shoulders 25 itself. The base of the groove 26 is U-shaped so that the remaining fins broaden towards the changing frame 8b.

In the case of the variant shown in FIG. 7, the groove base 27 of the groove 26 is V-shaped. In this case, too, the remaining fins broaden outwards towards the changing frame 8b.

In the case of the third variant shown in FIG. 8, two cooling grooves 26 are provided side by side, said cooling grooves being deeper than the support shoulder 25. A cooling web 28 remains between the two grooves 26.

FIG. 6 to 8 show also clearly that the discs 6 and 7 have, on their respective outer edge, a bevel facing the end faces of the support shoulder 25. This has the effect that a space having a triangular cross-section is formed between the support shoulder and the disc. This space has respectively inserted therein a sealing ring 12.

In the case of the third embodiment, the discs 6 and 7 are fastened by means of two press rings 29 pressing the discs 6 and 7 against the end faces of the support shoulder 25. On their respective outer edge facing away from the discs 6, 7, the press rings 29 are provided with a slight bevel 30. The end face of the changing frame 8b, which externally surrounds said press rings 29, is provided with a circumferentially extending groove 31 on both sides thereof, said circumferentially extending groove being radially spaced from the press ring in such a way that a crimped web 32 remains at the radially inner edge of the changing frame 8b. This arrangement can be seen in detail in FIG. 9a and 9b. In FIG. 9a, the press ring 29, though inserted, is not yet fastened by the crimped web. FIG. 9b shows the crimped web 32 which engages behind the bevel 30 of the press ring 29.

In the following, the mode of operation of the third embodiment will be explained in detail.

The irradiation device is operated in the same manner as in the case of the embodiments described hereinbefore.

The water contained between the discs 6 and 7 is cooled by dissipating the heat into the changing frame 8b via the surface of the support shoulder 25 which is enlarged by the cooling grooves 26. From the changing frame 8b, the heat is then transmitted — via a comparatively large contact surface — to the outer frame member 8a and from said outer frame member to the cooling fins. The filter 5 can easily be exchanged by loosening the knurled screws 24. In view of the large contact surface between the outer frame 8a and the changing frame 8b, the exchangeability does not impair in any way a good dissipation of heat from the filter 5.

Although the irradiation device was described on the basis of a cylindrical housing and, consequently, also on the basis of a circular filter in the case of the present embodiments, it is also possible to provide the filter with a rectangular structural design or with a structural design having the form of another polygon.

What is claimed is:

1. An irradiation device comprising a radiation source arranged within a housing and a filter arranged in the path of the rays of said irradiation source, two transparent and essentially plane-parallel discs supported within said housing by a frame and defining therebetween a sealed hollow space containing a medium which selectively influences the spectrum of said rays, outwardly projecting cooling fins arranged on the outer circumference of said frame and extending from the frame to a surrounding portion of the housing, at least one of said discs being flexible to accommodate expansion of said medium between the discs during use of the device.

2. An irradiation device according to claim 1, characterized in that the frame is made of metal or of some other material with good thermal conductivity.

3. An irradiation device according to claim 1, characterized in that the frame has a two-piece structural design comprising an outer frame member, which supports the cooling fins, and a changing frame, which is replaceably held in said outer frame member and which has secured thereto the discs.

4. An irradiation device according to claim 3, characterized in that the changing frame is provided with an inwardly projecting, circumferentially extending support shoulder, said support shoulder projecting between the discs and said discs abutting on said support shoulder.

5. An irradiation device according to claim 4, characterized in that the support shoulder has provided therein at least one circumferentially extending cooling groove opens towards the interior space between the discs.

6. An irradiation device according to claim 5, characterized in that two cooling grooves are provided side by side in the support shoulder, said cooling grooves being separated by a cooling web.

7. An irradiation device according to claim 5, characterized in that the depth of the cooling groove is at least equal to that of the support shoulder.

8. An irradiation device according to claim 5, characterized in that the groove base of the cooling groove is V-shaped or U-shaped.

9. An irradiation device according to claim 4, characterized in that the discs are each held by press ring, said press ring pressing the respective disc against one side of the support shoulder.

10. An irradiation device according to claim 4, characterized in that, on their respective outer edge facing the support shoulder, the discs are provided with a bevel, and that a sealing ring is arranged between said bevel and said support shoulder.

11. An irradiation device according to claim 1, characterized in that on the outer edge of each disc is a press ring, each press ring facing away from the respective disc is slightly beveled, and that a circumferentially extending groove is provided in the outer end face of the frame, which surrounds the press rings, in such a way that a crimped web is left.

12. An irradiation device according to claim 1, characterized in that the discs consist of flexible material.

13. An irradiation device according to claim 1, characterized in that the discs consist of polycarbonate.

14. An irradiation device according to claim 1, characterized in that the frame has attached thereto lamellae, which extend inwards between the discs and which are immersed in the medium.

15. An irradiation device according to claim 1, characterized in that the housing has a substantially tubular structural design, and that the frame has the outer ends of its cooling fins inserted into the housing such that air flow openings are kept free.

16. An irradiation device according to claim 1, characterized in that a fan is provided in the housing.

17. An irradiation device according to claim 16, characterized in that the fan is arranged on the side of the radiation source facing away from the filter.

18. An irradiation device according to claim 1, characterized in that an annular flow deflection means is arranged concentrically with the housing between the disc of the filter facing the radiation source and said radiation source, the flow inlet of said flow deflection means facing the cooling fins of the frame, whereas its flow outlet is directed towards the filter.

19. An irradiation device according to claim 18, characterized in that the flow deflection means has the structural design of a torus half whose outer edge abuts on the inner wall of the housing and whose inner edge is directed towards the filter.

20. An irradiation device according to claim 18, characterized in that the cooling fins are lengthened towards the interior of the housing, and that the flow deflection means is constructed as a cylindrical ring connecting the base portions of the cooling fins, said ring being closed with respect to the housing by means of a flange member and being arranged in spaced relationship with the inner disc of the filter so as to form the flow outlet.

21. An irradiation device according to claim 1, characterized in that a heat-resistant glass plate is arranged concentrically with the housing between the radiation source and the filter, the edge of said glass plate being spaced from the inner wall of said housing by means of an essentially closed annular gap.

22. An irradiation device according to claim 21, characterized in that the inner diameter of the annular gap exceeds the diameter of the inner edge of the flow deflection means.

23. An irradiation device according to claim 1, characterized in that the radiation source is a halogen lamp with a reflector directed towards the filter.

* * * * *